(12) United States Patent
Casonato

(10) Patent No.: US 8,709,172 B2
(45) Date of Patent: Apr. 29, 2014

(54) WASHING APPARATUS

(75) Inventor: Ottorino Casonato, Castelfranco Veneto (IT)

(73) Assignee: Steelco SpA, Riese Pio X (IT)

( * ) Notice: Subject to any disclaimer, the term of this patent is extended or adjusted under 35 U.S.C. 154(b) by 806 days.

(21) Appl. No.: 12/670,106

(22) PCT Filed: Jul. 25, 2008

(86) PCT No.: PCT/EP2008/059777
§ 371 (c)(1),
(2), (4) Date: Jan. 21, 2010

(87) PCT Pub. No.: WO2009/016111
PCT Pub. Date: Feb. 5, 2009

(65) Prior Publication Data
US 2010/0170544 A1      Jul. 8, 2010

(30) Foreign Application Priority Data
Jul. 27, 2007   (IT) .............................. UD2007A0135

(51) Int. Cl.
*A47L 15/24*        (2006.01)
(52) U.S. Cl.
USPC ......... 134/57 D; 134/152; 134/196; 134/197; 134/145
(58) Field of Classification Search
USPC ................ 134/137–138, 142, 143, 146, 165, 134/169 R, 175, 24, 42, 50, 57 D, 58 D, 134/196–197; 285/145.1, 145.5, 332; 239/392, 397, 456
See application file for complete search history.

(56) References Cited

U.S. PATENT DOCUMENTS

| | | | |
|---|---|---|---|
| 3,017,892 A | | 1/1962 | Mixon |
| 3,463,173 A | * | 8/1969 | Goldman ...................... 134/145 |
| 3,511,252 A | | 5/1970 | Kennedy |
| 3,568,691 A | * | 3/1971 | Kennedy et al. .............. 134/144 |

(Continued)

FOREIGN PATENT DOCUMENTS

| | | |
|---|---|---|
| DE | 29 19 140 A1 | 11/1980 |
| DE | 2919140 A * | 11/1980 |

(Continued)

OTHER PUBLICATIONS

Notice of Opposition to a European Patent, Apr. 12, 2013.

*Primary Examiner* — Michael Barr
*Assistant Examiner* — Kevin G Lee
(74) *Attorney, Agent, or Firm* — Novak Druce Connolly Bove + Quigg LLP

(57) ABSTRACT

Washing apparatus includes a washing chamber having two lateral walls, bottom wall and upper wall, and at the front an aperture for inlet and/or outlet; a main distribution circuit to distribute treatment fluid inside the chamber; a trolley-type movement device, insertable into the chamber, including a frame to support objects to be subjected to a washing cycle in the chamber and on which treatment fluid distribution elements are mounted. The frame formed by hollow tubular elements functioning as a secondary distribution circuit of washing liquid towards the distribution elements; a connector element located on a frame upper part as a secondary distribution circuit delivery element; and a hydraulic connection pipe mounted on the upper wall, to connect hydraulically the main distribution circuit to the secondary distribution circuit connector element, selectively movable vertically between a first position connected to the connector element and a second position separate from the connector element.

23 Claims, 2 Drawing Sheets

(56) References Cited

U.S. PATENT DOCUMENTS

| | | | |
|---|---|---|---|
| 3,590,863 A | | 7/1971 | Faust et al. |
| 3,612,077 A | * | 10/1971 | Capro .................. 134/123 |
| 3,837,917 A | * | 9/1974 | Jenkins et al. ............. 134/144 |
| 3,951,684 A | | 4/1976 | LaPrad et al. |
| 3,969,137 A | | 7/1976 | Jenkins et al. |
| 4,708,153 A | * | 11/1987 | Hambleton et al. ......... 134/170 |
| 5,087,081 A | | 2/1992 | Yoon |
| 5,427,129 A | * | 6/1995 | Young et al. .............. 134/176 |
| 5,771,909 A | * | 6/1998 | Hein et al. ............... 134/57 D |
| 6,102,054 A | * | 8/2000 | Diaz .................... 134/57 R |
| 6,401,771 B1 | * | 6/2002 | Kondo et al. .............. 141/90 |
| 6,510,858 B1 | | 1/2003 | Halstead et al. |
| 2006/0011220 A1 | * | 1/2006 | Mueller ................. 134/45 |

FOREIGN PATENT DOCUMENTS

| | | | |
|---|---|---|---|
| DE | 30 18 050 A1 | | 11/1981 |
| DE | 3018050 A | * | 11/1981 |
| DE | 3413386 A1 | | 10/1985 |
| DE | 196 27 762 A1 | | 1/1998 |
| DE | 19627762 A1 | * | 1/1998 |
| EP | 0 631 755 A1 | | 1/1995 |
| FR | 2544606 A | * | 10/1984 |
| GB | 1 380 788 | | 1/1975 |
| IT | UD2005A000193 | | 5/2007 |
| IT | UD2006A000232 | | 4/2008 |
| IT | UD 2006A232 | * | 4/2008 |
| JP | 7-327909 | | 12/1995 |
| JP | 07327909 A | * | 12/1995 |
| JP | 8-66463 | | 3/1996 |

* cited by examiner

WASHING APPARATUS

CROSS-REFERENCE TO RELATED APPLICATIONS

This application is a §371 National Stage Application of International Application No. PCT/EP2008/059777, filed on 25 Jul. 2008, claiming the priority of Italian Patent Application No. UD2007A000135 filed on 27 Jul. 2007.

FIELD OF THE INVENTION

The present invention concerns an apparatus for washing trolley-type objects, for example trolleys, beds and other wheeled equipment, and objects in general disposed on trolleys, in a washing chamber, for example of the type used in the field of hospitals, or in the field of restaurants, for washing self-service trolleys, or those used in aircraft. By washing chamber, here and hereafter, we mean a chamber in which the trolley-type objects can be subjected to at least one of the following treatments which constitute a so-called washing cycle: pre-wash in cold and/or hot water, hot-water wash advantageously with detergents, rinse, disinfection by means of chemicals and/or heat-disinfection, with a possible final drying using air, hot air or other fluid.

BACKGROUND OF THE INVENTION

A washing apparatus is known, for washing and heat-disinfecting surgical instruments, laboratory instruments or other, contained in baskets carried by a trolley, container or other trolley-type movement device.

This known apparatus has a washing chamber of the oblong tunnel type, having an entrance door on the dirty side and optionally an exit door towards the clean side, and an inclinable support plane, substantially on the level of the bottom of the washing chamber, provided with two parallel runners along which the instrument-carrying trolley is inserted slidingly inside the washing chamber.

The known washing apparatus has a main distribution circuit for the washing liquid, provided with a pump and pipes that take the washing liquid inside the washing chamber.

In the known washing apparatus a plurality of distribution elements are provided, to distribute the washing liquid, and are disposed along the lateral and bottom walls, and the upper wall, to direct the flow of washing liquid towards the trolley.

The trolleys or containers used in these known washing apparatuses consist of a frame, which supports said baskets and which also supports a plurality of washing impellers. The frame is hollow inside and thus functions as a secondary distribution circuit of the washing liquid, putting a delivery element of washing liquid connected to the main distribution circuit into hydraulic communication with said impellers.

Moreover, a hydraulic pipe is provided, and is part of the main distribution circuit and disposed on the level of the support plane, laterally or below on the bottom of the washing chamber. The pipe is selectively connected to the delivery element of the secondary distribution circuit of the washing liquid provided on the trolley or container.

Once the trolley has been inserted and the doors closed, a control unit activates the connection of the pipe to the delivery element of the trolley and starts the washing cycle.

The movement of the trolleys from and to the apparatus is described for example in the Italian patent applications in the name of the present Applicant, UD2005A000193 and UD2006A000232.

The solution where the hydraulic pipe is disposed on the bottom of the washing chamber has the following disadvantages:
  interference of the hydraulic pipe with the impellers, which are thus eliminated or reduced in diameter, but to the detriment of productivity and the effectiveness of the wash;
  need to provide a lower compartment, made under the washing chamber, to house the hydraulic pipe and the auxiliary hydraulic and electric connections;
  risk of leakages of washing liquid from the lower compartment to the floor around the washing apparatus;
  reduced exploitation of most of the washing liquid in the delivery element, due to the contrasting action of the force of gravity during the thrust from the bottom upwards, with reduced outlet pressure to the impellers and possible inefficiency of the wash.

The solution where the hydraulic pipe is disposed laterally has the following disadvantages:
  risk of lateral interference with the baskets or the impellers;
  need for a counter-thrust element or member, on the side opposite that where the hydraulic pipe is connected, to prevent the trolley from moving or turning over once the pipe is connected;
  unequal distribution of the washing liquid in the secondary distribution circuit of the trolley, due to the lateral position of the delivery element, with consequent lack of homogeneity in the outlet pressure of the washing liquid to the impellers and possible inefficiency of the wash.

Purpose of the present invention is to achieve a washing apparatus which overcomes the disadvantages of the state of the art and which exploits effectively most of the washing liquid entering the secondary distribution circuit.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purpose, a washing apparatus according to the present invention comprises:
  a washing chamber delimited by two lateral walls, a bottom wall and an upper wall, and provided at the front with an inlet aperture for inlet and/or outlet;
  a main delivery circuit for a treatment fluid, able to distribute the treatment fluid inside the washing chamber;
  at least a trolley-type movement device, able to be selectively inserted into the washing chamber and comprising a frame able to support objects to be subjected to a washing cycle in the washing chamber and on which elements for the distribution of the treatment fluid are mounted.

The frame consists of hollow tubular elements to function as a secondary distribution circuit of the treatment fluid to the distribution elements.

According to a characteristic feature of the present invention, the washing apparatus comprises at least a connector element located on the upper part of the frame and which functions as a delivery element of the secondary distribution circuit, and a hydraulic connection pipe mounted on the upper wall.

The connection pipe is able to connect hydraulically the main delivery circuit to the connector element of the secondary distribution circuit and is selectively movable vertically between a first position connected to the connector element and a second position separated from the connector element.

By treatment fluid we mean a pre-wash, washing, rinsing or heat-disinfecting fluid or liquid, or a drying fluid, depending on the steps of the determinate washing cycle.

According to a variant, the invention comprises linear actuator means to move the hydraulic connection pipe, advantageously disposed on the upper wall.

The position of the trolley-type movement device is advantageously a pre-defined position, which allows the correct insertion and hydraulic coupling of the connector element and the hydraulic connection pipe.

To this purpose, according to a variant, a sensor means is provided, advantageously but not exclusively of a magnetic type, to detect the position of the trolley-type movement device.

The sensor means sends a signal indicating the position to a control unit which, on the basis of this, starts the linear actuator means and the washing cycle.

Thanks to the disposition on the upper wall of the hydraulic connection pipe, the washing apparatus exploits effectively most of the treatment fluid entering the secondary distribution circuit.

Moreover, the present invention does not produce any interference of the hydraulic pipe with the distribution elements, particularly in the variant with the impellers, allowing to size them correctly, thus increasing productivity and the effectiveness of the wash.

With the present invention there is no need to provide a lower compartment, made under the washing chambers, to house the hydraulic pipe and the auxiliary hydraulic and electric connections; on the contrary, these are disposed on the upper wall, exploiting a space that is normally unused and free.

The present invention also avoids the risk of leakages of treatment fluid to the floor surrounding the washing apparatus.

Since the hydraulic connection pipe directs the treatment fluid downwards, there is no contrast to the force of gravity and there is an effective exploitation of most of the treatment fluid in the delivery element, with optimum outlet pressure to the distribution elements and effective washing.

Moreover, the present invention does not cause lateral interference with the baskets or the distribution elements.

Furthermore, there is no need for a counter-thrust element or member, on the side opposite the one where said hydraulic pipe is connected, to prevent the trolley from moving or overturning once the pipe is connected. The vertical force of hydraulic coupling between the connection pipe and the connector element has the bottom of the washing chamber as a natural contrast.

An advantageous variant of the invention provides that the connector element is in a central position with respect to the secondary distribution circuit of the frame. This allows a uniform distribution of the treatment fluid in the secondary distribution circuit of the trolley, with a consequent homogeneity of the outlet pressure of the treatment fluid to the distribution elements, and a greater efficiency of the wash.

BRIEF DESCRIPTION OF THE DRAWINGS

These and other characteristics of the present invention will become apparent from the following description of a preferential form of embodiment, given as a non-restrictive example with reference to the attached drawings wherein.

DETAILED DESCRIPTION OF A PREFERENTIAL FORM OF EMBODIMENT

Figure 1:
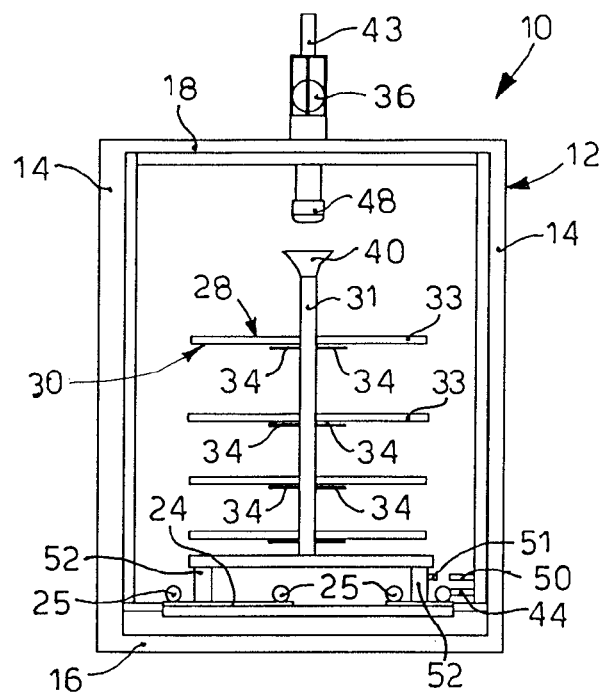
FIG. 1 is a schematic front view of a washing apparatus according to the present invention.

With reference to FIG. 1, a washing apparatus 10 according to the present invention comprises a washing chamber 12 suitable for washing and heat-disinfecting surgical instruments of a known type and not shown in the drawings.

The washing chamber 12 is of the oblong tunnel type and is delimited by two lateral walls 14, a bottom wall 16 and an upper wall 18, and is also provided with access apertures 20, 22, closed by means of doors of a known type and not shown in the drawings, for example of the sliding type. A first aperture 20, disposed on the front side (FIG. 2), is used for access to the washing chamber 12 from the "dirty" side, that is, before washing.

A second aperture 22, disposed on the rear side, is used for outlet from the washing chamber 22 on the clean side.

On the bottom wall 16 a support plane 23 is also fixed, inclinable laterally and provided with two parallel runners 24 delimited by respective guide bars 25. The runners 24 are suitable for the sliding insertion into the chamber 12 of trolleys 28 or other trolley-type movable devices.

The apparatus 10 also comprises a primary hydraulic circuit 26 able to distribute the washing liquid inside the washing chamber 12. The primary circuit 26 is connected to a series of tubular washing lances 21 of a known type, disposed inside the chamber 12, laterally, on the bottom and at the top, of which only the upper ones are shown in the drawings.

The apparatus 10 also comprises at least a trolley 28 able to support baskets, of a known type and not shown in the drawings, in which the surgical instruments to be sent for washing are placed, and able to be selectively inserted into the washing chamber 12.

Figure 2:
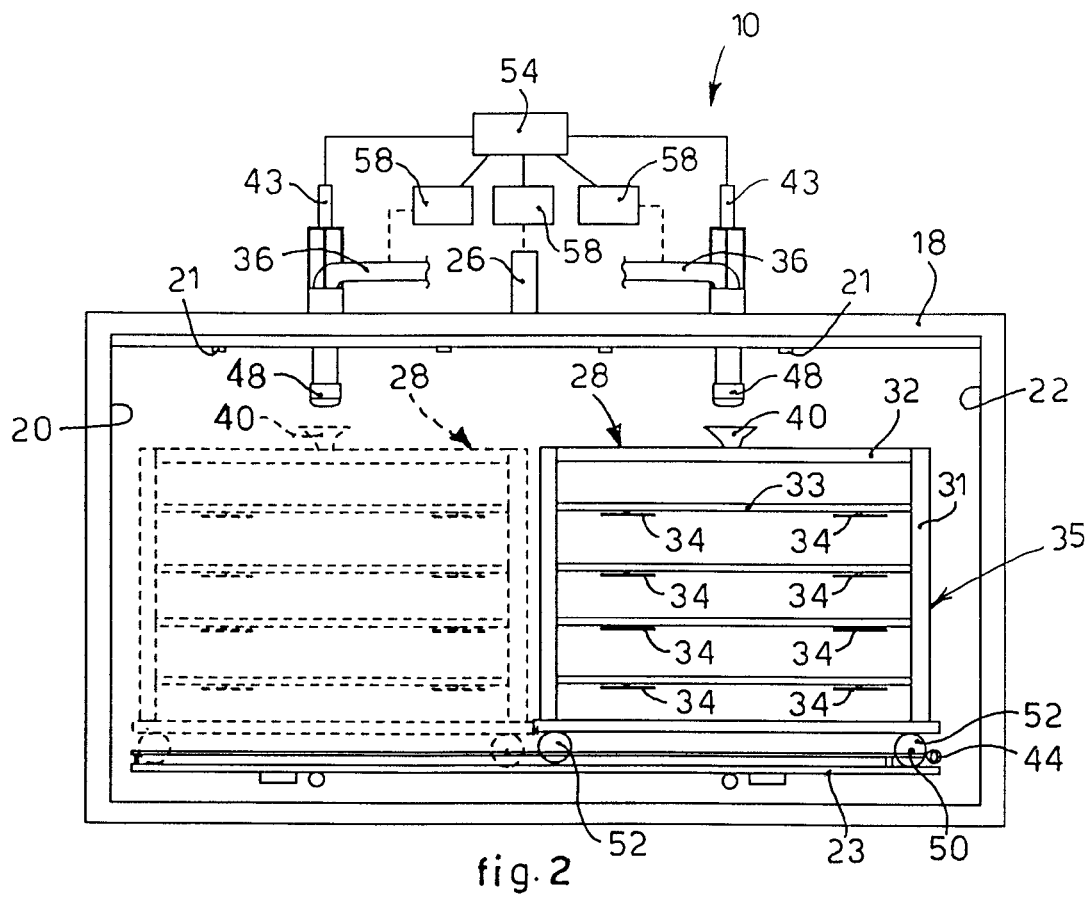
FIG. 2 is a schematic lateral view of the apparatus in FIG. 1.

In this case the washing chamber 12 is pre-disposed and sized to accommodate, during a single washing cycle, two trolleys 28 lined up, of which FIG. 2 shows a first with a continuous line and a second with a discontinuous line.

Each trolley 28 comprises a frame 30 formed by two vertical uprights 31 connected at the upper part by means of a horizontal element 32. Four grid-type shelves 33 are also fixed horizontally on the frame 30, in order to support said baskets. Under each shelf 33 two washing impellers 34 are mounted. The uprights 31, the horizontal element 32 and the impellers 34, which have a tubular structure, are connected to each other internally so as to constitute a secondary hydraulic circuit 35 of the apparatus 10.

As an alternative to the impellers, fixed pipes can be used, with distribution nozzles.

The trolley 28 is provided with a funnel 40 attached centrally on the horizontal element 32, in a position symmetrical to the frame 30.

The bottom of the funnel 40 opens into the tubular structure of the horizontal element 32, thus functioning as main delivery element to introduce the washing liquid into the secondary hydraulic circuit 35.

The primary circuit 26 is provided with two hydraulic connection pipes 36, which are able to be inserted into the respective funnels 40 of the trolleys 28 and connected hydraulically to the latter.

In particular, the pipes 36 are positioned on the upper wall 18 of the washing chamber 12, substantially at the center of the two halves of the chamber 12, as can be seen in FIG. 2, in a position coordinated for insertion into the respective funnels 40 of the trolleys 28.

The hydraulic connection pipe 36 is thus able to effect a selective hydraulic connection between the primary hydraulic circuit 26 and the secondary hydraulic circuit 35.

To this purpose, the pipe 36 is made selectively movable between a first position in which it is connected hydraulically to the funnel 40 and a second position in which the pipe 36 is distanced and separated from the funnel 40.

Figure 3:
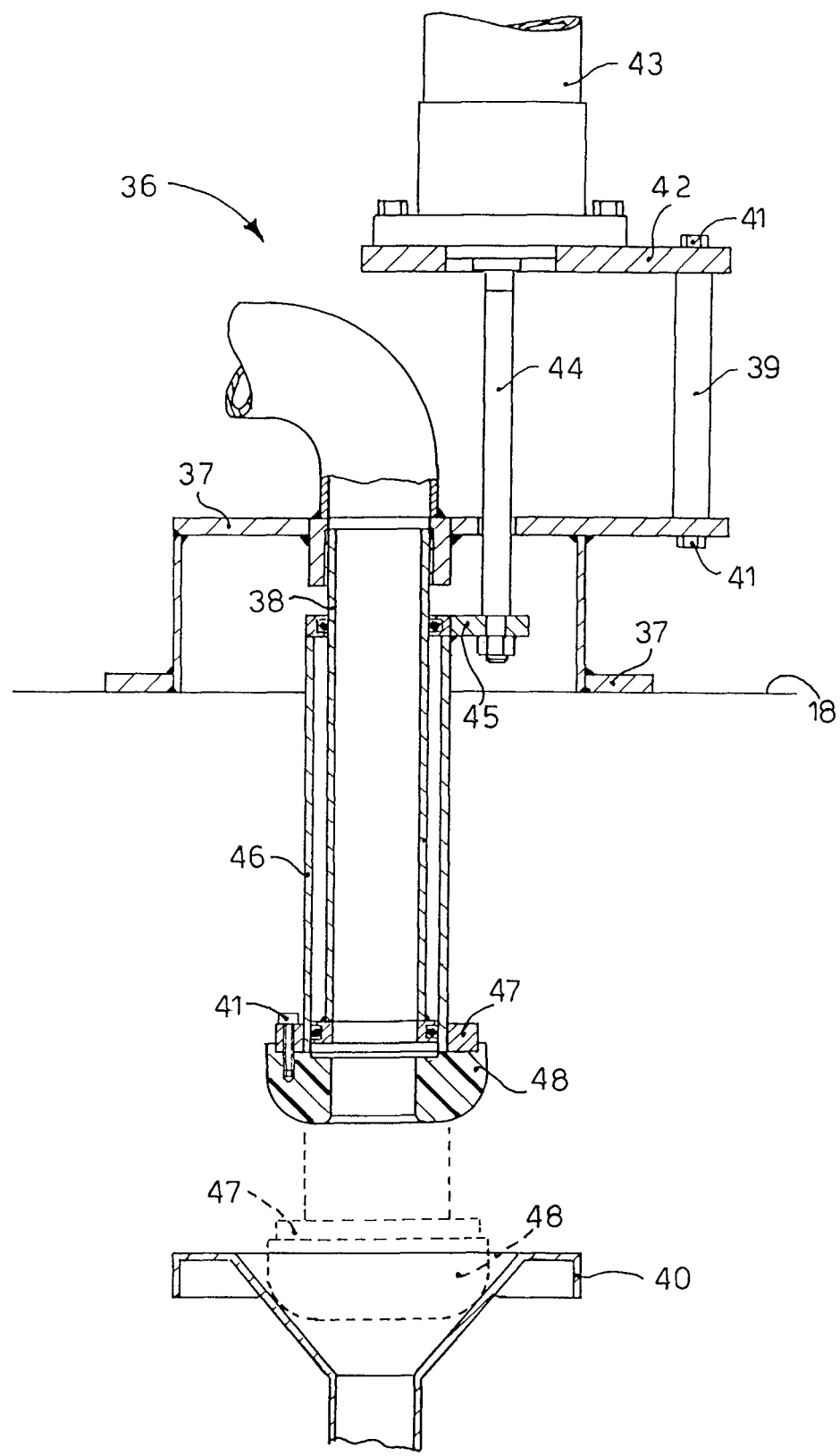
FIG. 3 is a partial section of a part of the apparatus in FIG. 1.

According to a preferential embodiment, the connection pipe 36 is of the telescopic type, and comprises (FIG. 3) a fixed part 38 and a part 46 movable vertically with respect to the upper wall 18 of the chamber 12, inside the latter.

The fixed part 38 is fixed, by means of a flange 37, to the upper wall 18, outside the chamber 12 and connects to the primary hydraulic circuit 26. Spacer elements 39 are provided, mounted externally on the flange 37, attached with bolts 41 and able to support a support element 42 for a pneumatic linear actuator 43, provided with a piston 44 selectively movable vertically, of a known type.

The movable part 46 of the pipe 36 is connected, by means of a joint element 45, to the piston 44 so as to be moved, in a substantially vertical manner, towards the inside of the washing chamber 12 and vice versa.

The movable part 46 is provided with a circular crown 47, towards the inside of the chamber 12, on which a pipe union 48, made of POM, Teflon or other plastic material with similar properties is mounted coaxially and is able to be inserted into the funnel 40 for hydraulic connection. The pipe union 48 has a substantially cylindrical shape with a connection profile between the lateral surface and the lower surface, rounded so as to allow an effective coupling with the funnel 40. Alternatively, the pipe union 48 is conical, shaped like a truncated cone or other suitable shape.

The coupling of the pipe union 48 with the funnel 40 requires a pre-defined position of the trolley 28 inside the washing chamber 12.

In this pre-defined position the funnel 40 and the pipe union 48 are substantially aligned vertically.

To preliminarily define the position of the first trolley 28 that is inserted into the chamber 12, a horizontal end-of-travel pin 56 is provided, located at one end of the runner 24, in correspondence with the aperture 22 so as to clamp the trolley 28. The pin 56 is able to be moved perpendicularly to the wall 14, between a first position in which it is positioned more displaced towards the center of the washing chamber 12, so as to occupy the relative runner 24 and interfere with a portion of the trolley 28, and a second position in which it is positioned retracted, towards the wall 14, so as not to interfere with the trolley 28.

In order to determine the exact positioning of the trolleys 28 inside the washing chamber 12, the apparatus 10 also comprises magnetic position sensors 50 of a known type, in this case two, each of which is associated with a corresponding permanent magnet 51 mounted on each trolley 28.

According to a preferential embodiment the magnets 51 are attached in correspondence with a front wheel 52 of each trolley 28.

The magnetic sensors 50 are disposed in correspondence with the bar 25 facing towards the wall 14 that delimits one of the runners 24, in the pre-defined position corresponding to the position taken by the trolleys 28 for the correct coupling between the funnel 40 and the corresponding pipe union 48.

The position of the second trolley 28 is automatically defined when the latter is lined up and abuts on the first trolley 28.

The apparatus 10 also comprises a programmable control unit 54, able to control the washing cycle.

Said magnetic sensors 50, and the pneumatic actuation device 43 to control them coherently with the washing cycle, are all connected to the control unit 54.

The control unit 54 also commands the movement of the end-of-travel pin 56.

The apparatus 10 also comprises a multi-way valve device 58 of a known type, able to selectively convey the flows of washing liquid in the hydraulic circuits 26 and 35 of the apparatus 10. In this case the multi-way valve device 58 comprises three valves, two of which associated with each hydraulic connection pipe 36 and the third valve associated with the primary hydraulic circuit 26. The valve device 58 is commanded by said control unit 54, so as to selectively activate the flows of washing liquid in the hydraulic circuits 26 and 35, according to the pre-determined washing program.

The apparatus 10 as described heretofore functions as follows.

At the start of a new washing cycle at least a first trolley 28, on which the baskets are disposed with the surgical instruments to be washed, is pushed inside the washing chamber 12 from the "dirty" side of the chamber 12, as far as the position in which the wheel 52 is stopped by the pin 56, suitably positioned in said first position. The first trolley 28 is therefore disposed in the pre-defined position, in which the magnet 51 is in a position coordinated with the magnetic position sensor 50, which signals to the control unit 54 that the trolley 28 is present and correctly positioned.

In this case a second trolley 28 is positioned inside the chamber 12, queuing behind the first trolley 28. The correct disposition of the second trolley 28 in the chamber 12 is determined by the pre-defined position of the first trolley 28. In fact, the second trolley 28, thrust up against the first trolley 28 already inserted, and stopped by the pin 56, is already disposed in its pre-defined position.

When the positioning of the trolley 28 is complete, an operator starts the washing cycle of the apparatus 10. The control unit 54 activates the command to close the access door on the "dirty" side and, by means of the pneumatic device 43 associated with the trolley 28, commands the movable part 46 of the hydraulic connection pipe 36 to move by pushing the pipe union 48 against the funnel 40. During the washing cycle, the pneumatic device 43 exerts a constant vertical thrust able to maintain the pipe union 48 inserted and hydraulically coupled in the funnel 40.

The control unit 54 starts the washing cycle by activating, simultaneously or in sequence in selective manner, the delivery valves of the multi-way valve device 58. The washing liquid exiting from the hydraulic connection pipe 36 is introduced into the secondary hydraulic circuit 35 of the trolley 28 by means of the funnel 40 and exits from the washing impellers 34.

At the end of the washing cycle the control unit 54 commands the movable part 46 of the hydraulic connection pipe 36 to be raised, and hence the pipe union 48 is separated from the funnel 40 and the pin 56 is displaced into said second position. In this way, once the sliding door has been opened in correspondence with the second aperture 22 on the "clean" side, the trolley 28 is removed from the washing chamber 12.

The movement of the trolleys 28 can be of the manual type or automated, as shown in the Italian patent applications in the name of the present Applicant UD2005A000193 and UD2006A000232.

The washing chamber 12 can be sized to accommodate a single trolley 28, or two or more than two trolleys 28.

Furthermore, the washing chamber 12 can have two apertures 20, 22 and two related doors, first-in, first-out cycle, or a single aperture 20 or 22 with a single door through which the trolleys 28 enter and exit, last-in first-out cycle.

Another variant provides to feed two trolleys 29 or more in parallel.

It is clear that modifications and/or additions of parts may be made to the washing apparatus 10 as described heretofore, without departing from the field and scope of the present invention.

For example, immediately downstream of the funnel 40, and inside the horizontal element 32, an element to divert the flow may be disposed, provided with a rounded profile able to convey more efficiently the movement of the fluid entering into the secondary hydraulic circuit 36. In this way it is possible to reduce the loss of quantities of motion and hence pressure, due to the impact of the fluid with the internal wall of the horizontal element 32, after it has been introduced into the secondary hydraulic circuit 35. This leads to a more efficient wash which allows, for example, to reduce the time needed to carry out the washing cycles and therefore leads to an increase in productivity.

It is also clear that, although the present invention has been described with reference to some specific examples, a person of skill in the art shall certainly be able to achieve many other equivalent forms of washing apparatus, having the characteristics as set forth in the claims and hence all coming within the field of protection defined thereby.

The invention claimed is:

1. A washing apparatus comprising:
    a washing chamber delimited by two lateral walls, a bottom wall and an upper wall, provided at the front with an inlet aperture for inlet and/or outlet;
    a main distribution circuit for a treatment fluid, configured to distribute the treatment fluid inside the washing chamber;
    at least a trolley-type movement device configured to be removably inserted into said washing chamber via said inlet aperture and comprising a frame configured to support objects to be subjected to a washing cycle in the washing chamber and on which distribution elements for the treatment fluid are mounted, said frame being formed by hollow tubular elements functioning as a secondary distribution circuit for the washing liquid to the distribution elements,
    at least a connector element located on the upper part of the frame and which functions as a delivery element for delivering treatment fluid to the secondary distribution circuit,
    a hydraulic connection pipe mounted on said upper wall, which is configured to hydraulically connect the main distribution circuit to the connector element of the secondary distribution circuit, said hydraulic connection pipe being vertically movable between a first position connected to the connector element and a second position separated from the connector element, said hydraulic connection pipe having a movable part and a fixed part with respect to said upper wall of said chamber; and
    a linear actuator configured to move the hydraulic connection pipe between the first position connected to the connector element and the second position separated from the connector element, wherein said linear actuator has a piston configured to move the hydraulic connection pipe, wherein said piston is axially offset from said movable part and is connected to said movable part by a joint element.

2. The washing apparatus as in claim 1, wherein the connector element is located in a central position with respect to the secondary distribution circuit of the frame.

3. The washing apparatus as in claim 1, comprising a position sensor configured to detect the position of the trolley-type movement device.

4. The washing apparatus as in claim 1, comprising a control unit configured to control the washing cycle.

5. The washing apparatus as in claim 4, further comprising a linear actuator configured to move the hydraulic connection pipe, wherein the control unit is configured to control the action of the linear actuator according to the washing cycle.

6. The washing apparatus as in claim 4, further comprising a linear actuator configured to move the hydraulic connection pipe, and a position sensor configured to detect the position of the trolley-type movement device, wherein the control unit is connected to the position sensor, from which the control unit receives a signal indicating the position of the trolley-type movement device to activate the linear actuator when the trolley-type movement device is in a pre-defined position.

7. The washing apparatus as in claim 6, wherein the pre-defined position of the trolley-type movement device is determined by a substantial alignment of the hydraulic connection pipe and the connector element.

8. The washing apparatus as in claim 6, wherein a stopping mechanism is provided to stop the trolley-type movement device in said pre-defined position.

9. The washing apparatus as in claim 1, comprising two or more trolley-type movement devices, each of which has a respective connector element associated with a corresponding hydraulic connection pipe, a multi-way valve mechanism being provided to selectively feed the treatment liquid to one or another of the hydraulic connection pipes, said multi-way valve mechanism being controlled by a control unit according to the washing cycle.

10. The washing apparatus as in claim 1, wherein the distribution elements comprise washing impellers.

11. The washing apparatus as in claim 1, wherein the distribution elements comprise fixed pipes provided with distribution nozzles.

12. The washing apparatus as in claim 1, comprising an element to divert the flow of treatment fluid, located downstream of the connector element.

13. The washing apparatus as in claim 4, further comprising a linear actuator able to move the hydraulic connection pipe, wherein the control unit is able to control the action of the linear actuator according to the washing cycle.

14. The washing apparatus as in claim 5, further comprising a position sensor configured to detect the position of the trolley-type movement device, wherein the control unit is connected to the position sensor, from which the control unit receives a signal indicating the position of the trolley-type movement device to activate the linear actuator when the trolley-type movement device is in a pre-defined position.

15. The washing apparatus as in claim 7, wherein a stopping mechanism is provided to stop the trolley-type movement device in said pre-defined position.

16. The washing apparatus as in claim 1, wherein said frame comprises a plurality of shelves, said plurality of shelves having a plurality of treatment fluid distribution elements forming part of said secondary distribution circuit.

17. The washing apparatus as in claim 1, wherein said connector element comprises a funnel.

18. The washing apparatus as in claim 17, wherein said funnel is centrally attached to a horizontal tubular element of the frame.

19. The washing apparatus as in claim 1, wherein the linear actuator comprises a pneumatic device providing vertical thrust to said connection pipe to maintain said first position.

20. The washing apparatus as in claim 1, wherein said fixed part is coupled to said upper wall, and connects to said main distribution circuit, at a position outside said chamber.

21. The washing apparatus as in claim 8, wherein said stopping mechanism comprises a horizontal end-of-travel pin movable between a first position towards a center of the chamber, wherein said end-of-travel pin interferes with movement of said trolley-type movement device, and a second position in which said end-of-travel pin is retracted away from the center of the chamber so as not to interfere with said trolley-type movement device.

22. The washing apparatus as in claim 6, wherein said position sensor comprises at least one magnetic position sensor disposed at a position at which it will detect a magnet mounted on said trolley-type movement device when said trolley-type movement device is in said pre-defined position.

23. A washing apparatus, comprising:
- a washing chamber delimited by two lateral walls, a bottom wall and an upper wall, provided at the front with an inlet aperture for inlet and/or outlet;
- a main distribution circuit for a treatment fluid, configured to distribute the treatment fluid inside the washing chamber;
- at least a trolley-type movement device configured to be removably inserted into said washing chamber via said inlet aperture and comprising a frame configured to support objects to be subjected to a washing cycle in the washing chamber and on which distribution elements for the treatment fluid are mounted, said frame being formed by hollow tubular elements functioning as a secondary distribution circuit for the washing liquid to the distribution elements,
- at least a connector element located on the upper part of the frame and which functions as a delivery element for delivering treatment fluid to the secondary distribution circuit,
- a hydraulic connection pipe mounted on said upper wall, which is configured to hydraulically connect the main distribution circuit to the connector element of the secondary distribution circuit, said hydraulic connection pipe being vertically movable between a first position connected to the connector element and a second position separated from the connector element, and having a movable part and a fixed part with respect to said upper wall of said chamber; and
- a linear actuator configured to move the hydraulic connection pipe between the first position connected to the connector element and the second position separated from the connector element, wherein said connector element comprises a funnel and said movable part is provided with a pipe union configured to be inserted and coupled into the funnel for hydraulic connection, and wherein said linear actuator has a piston configured to move the hydraulic connection pipe, wherein said piston is axially offset from said movable part and is connected to said movable part by a joint element.

* * * * *